United States Patent [19]

Möll et al.

[11] Patent Number: 5,981,300

[45] Date of Patent: Nov. 9, 1999

[54] TEST KIT FOR ANALYZING BODY FLUIDS AND ANALYSIS METHOD

[75] Inventors: Claus-Jürgen Möll, Moers; Theodor Paessens, Kalkar; Jörg Althoff, Greven, all of Germany

[73] Assignee: M & M Dental-Medizin GmbH, Moers, Germany

[21] Appl. No.: 08/849,659

[22] PCT Filed: Dec. 7, 1995

[86] PCT No.: PCT/EP95/04812

§ 371 Date: May 29, 1997

§ 102(e) Date: May 29, 1997

[87] PCT Pub. No.: WO96/18902

PCT Pub. Date: Jun. 20, 1996

[30] Foreign Application Priority Data

Dec. 16, 1994 [DE] Germany ............................ 4444764

[51] Int. Cl.⁶ .................................................. G01N 33/48
[52] U.S. Cl. .............................. 436/811; 422/57; 422/58; 422/61; 436/810
[58] Field of Search ................................ 422/58, 61, 56, 422/57; 436/810–811

[56] References Cited

U.S. PATENT DOCUMENTS

| 3,701,633 | 10/1972 | Davis . |
| 3,746,624 | 7/1973 | Hoerman et al. . |
| 4,582,795 | 4/1986 | Shibuya et al. . |
| 4,654,309 | 3/1987 | Mlinar . |
| 4,976,951 | 12/1990 | Rosenberg et al. . |
| 5,357,989 | 10/1994 | Gathani . |

FOREIGN PATENT DOCUMENTS

| 0097904 | 1/1984 | European Pat. Off. . |
| 0 418 739 A1 | 3/1991 | European Pat. Off. . |
| 0 442 231 A1 | 8/1991 | European Pat. Off. . |
| WO 91/14000 | 9/1991 | WIPO . |

*Primary Examiner*—Lyle A. Alexander
*Attorney, Agent, or Firm*—Herbert Dubno; Jonathan Myers

[57] ABSTRACT

A test kit is disclosed for analyzing a patient's saliva to determine the patient's risk of tooth decay, which contains: (a) a support; (b) an absorbent material in contact with said support and capable of removing saliva from the mouth and of absorbing the saliva; (c) a composition coated on said absorbent material, said composition soluble in saliva and capable of reaction inside the mouth of the patient with the saliva to reduce the pH of the saliva; and (d) a color scale for determining outside of the mouth of the patient the pH of the saliva absorbed by the absorbent material in which the composition is dissolved to measure the reaction of the composition with the saliva in the patient's mouth to determine the patient's risk of tooth decay.

17 Claims, 3 Drawing Sheets

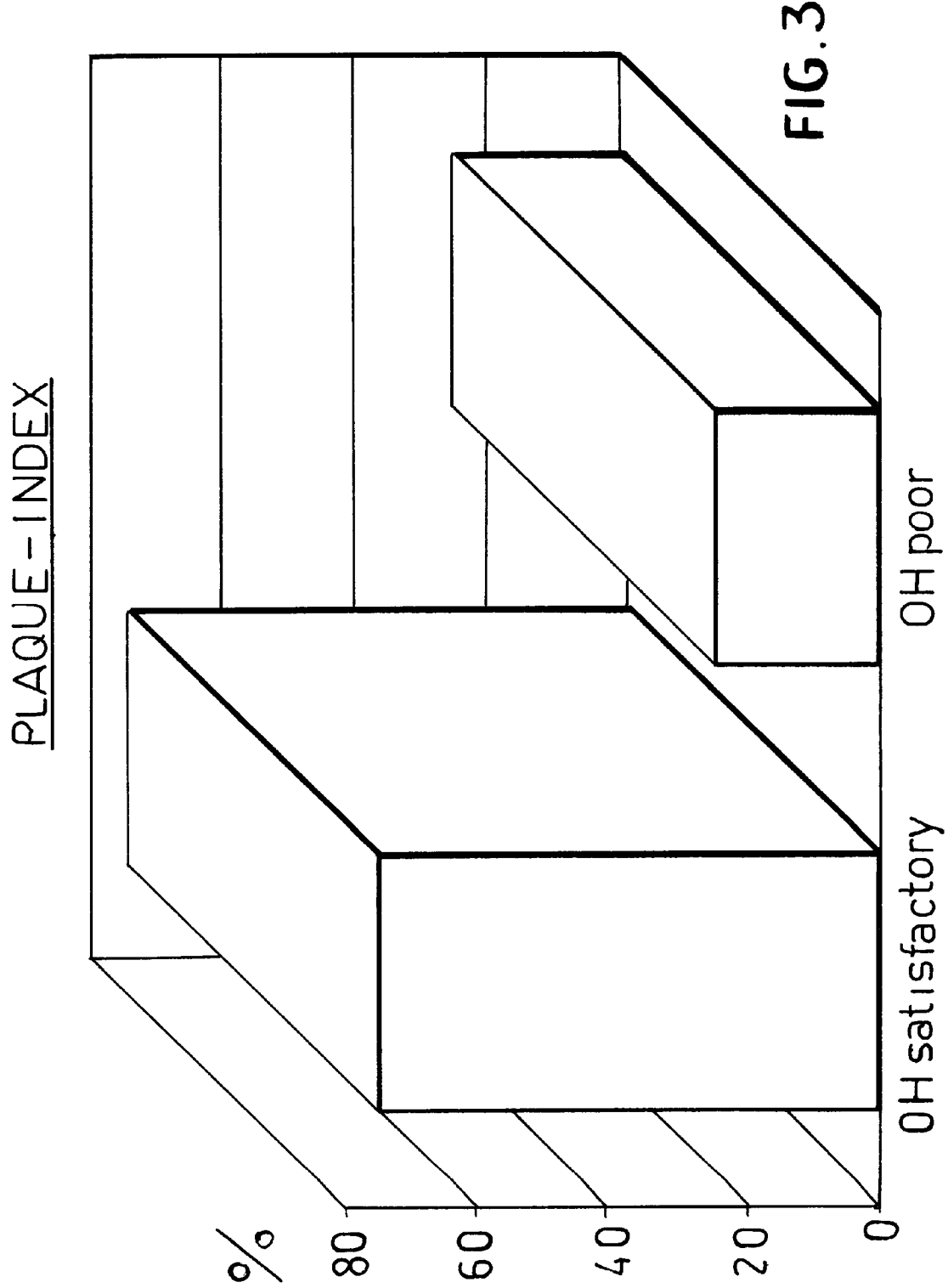

TEST KIT FOR ANALYZING BODY FLUIDS AND ANALYSIS METHOD

FIELD OF THE INVENTION

This invention relates to a test kit for analyzing body fluids, more particularly saliva.

BACKGROUND OF THE INVENTION

The prevention of tooth decay involves regular examinations at the dentist, a six-month check-up generally being recommended. However, this advice is often not heeded because the layman is not aware of his own personal risk of tooth decay and often mistakenly believes that, in his case this risk is minimal.

Accordingly, it would be useful to have a test which could be carried out by the layman himself and which would provide information as to his own personal risk of tooth decay in a simple, quick and inexpensive manner.

The exact causes of tooth decay and the processes involved have not yet been fully explained. What is certain, however, is that tooth decay is linked to the presence of microorganisms and carbohydrates in the oral cavity. The fermentation of carbohydrate-containing food residues which adhere to the teeth results in acidification of the surrounding medium, through formation of the degradation product lactic acid and hence in the dissolution of inorganic salts from the dental hard tissue. Microorganisms are able to migrate into the loosened hard tissue where they attack the organic supporting tissue of the teeth. Tooth decay begins above all in plaque-affected areas.

Investigations by the inventors have shown that the analysis of saliva, particularly in regard to its pH value, can provide information on the risk of tooth decay, as explained in more detail in the following.

Saliva tests and means for removing saliva for analysis purposes have been known for some time. One such process is described in DE 36 32 303 A1. In this process, an elastic, absorbent, inert substance is chewed by the volunteer and then introduced into a centrifuge tube provided with a perforated base. Like many other known processes, however, this process is only suitable for dental clinics and cannot readily be carried out by the layman.

In addition, a mouth swab for oral hygiene is known from the prior art (DE 37 09 497 A1). Arranged at one end of the supporting stick of the mouth swab is a cottonwool bud impregnated with an oral treatment formulation. The treatment formulation is prevented from evaporating by a dry saliva-soluble polymeric coating of the swab so that the oral swab can be stored for long periods without becoming unusable. The coating material consists essentially of acrylic resin and does not contain any carbohydrates. In contrast to the present invention, however, the known oral swab is used to introduce liquid into the mouth and not to remove saliva.

DE 29 41 471 A1 describes a provocation test for tooth decay which uses a liquid test medium. The test medium itself contains not only the carbohydrate but also the pH indicator. The disadvantage of this test lies above all in its complexity. Thus, the tartar taken from the patient has to be incorporated in the test medium which then has to be observed for a change in color after incubation for a fixed period, for example 30 minutes.

U.S. Pat. No. 5,357,989 describes a tooth cleaning material, for example dental floss, which is impregnated or coated with a pH indicator. The subject matter of this document is not a provocation test but merely the measurement of the prevailing pH value.

Another water-based reagent for conducting a test for tooth decay similar to that disclosed in DE 29 41 471 A1 is described in detail in DE 30 48 705 A1. This is also a provocation test because the aqueous reagent solution may also contain sucrose. However, the disadvantage here is again the relatively long waiting time after introduction of the saliva into the test solution which is said to be about 30 minutes. Such a test is inconvenient and complicated for the layman.

EP 0 097 904 A1 uses a paper impregnated with sucrose and a pH indicator. To carry out the test, saliva is applied to this paper. This test also involves incubation for 20 to 30 minutes which is a major disadvantage for application by the layman.

Another test is described in WO 91/14000. The test kit consists of a support with a first porous zone, namely a filter paper impregnated with a color test substance. A second porous zone is impregnated with a color developer. For application, saliva is applied to the first zone after which the support is folded so that the two zones come into contact with one another. Here, too, the disadvantage is the need for incubation at a temperature of about 37° C. over a period of, typically, 15 minutes. The need for a certain minimum temperature alone makes this test impracticable for the layman.

The test according to U.S. Pat. No. 3,746,624 also involves incubation of the sample —in this case for about 48 hours in a solution.

Finally, U.S. Pat. No. 4,976,951 is cited. Here, a sugar-containing chewing gum is chewed for a certain time by the volunteer and is then washed and, finally, incubated in a special liquid for 6 to 24 hours at 35 to 37° C. A test such as this is very complicated for the layman to carry out.

OBJECT OF THE INVENTION

The object of the invention is to provide an inexpensive test kit for analyzing body fluids, more particularly saliva, which could be handled in a convenient, pleasant, simple, quick and safe manner by the layman and which would be suitable for a so-called provocation test.

SUMMARY OF THE INVENTION

According to the invention, this problem is solved by the test kit mentioned at the beginning which is characterized by a support with an absorbent material, more particularly dry surgical cottonwool, for removing the body fluid and a composition soluble in the body fluid and provoking a certain reaction of the body and/or its microorganisms and by a means for determining medically relevant properties of the body fluid removed, more particularly its pH value.

The test kit according to the invention is very quick, easy and pleasant to use by comparison with the prior art. The volunteer places a support, more particularly a sugar-containing support, in his mouth. No chemical indicator or other chemicals unpleasant to the layman have to be introduced into the mouth. There is no waiting—except for the pleasant sucking of the reaction-provoking mass in the case of the tooth decay test. The body fluid sample does not have to be incubated after removal. In contrast to the prior art, the necessary waiting time for the provoked reaction elapses during dissolution of the provoking mass in the body fluid, i.e. before the actual removal of the fluid by the absorbent material.

After the support has come into contact with the body fluid, the mass adhering thereto takes a certain time to dissolve. In the intervening period, that component of the mass which causes the body reaction is released and the body reacts characteristically thereto. The time in question can be determined in advance by suitably selecting the quantity and the composition of the mass so that the user does not have any timing to do. It is merely necessary to keep the support in contact with the body fluid until the mass has completely dissolved.

After the mass has dissolved, the body fluid is absorbed by the absorbent material and can be applied by means of the support to the means for determining medically relevant properties, for example by rolling the moist end of a stick on pH paper. By comparing the coloration with colored comparison boxes, the pH value of the saliva can be read off immediately, quickly and safely.

The mass is preferably in the form of a coating for the absorbent material. In one particular embodiment, the coating completely surrounds the absorbent material. On the one hand, this protects the generally sterile absorbent material. On the other hand, the absorbent material only absorbs the body fluid when part of the coating or even the entire coating has dissolved in the body fluid and a certain waiting time— in which the body and/or its microorganisms has/have reacted to the ingredients of the mass in the required manner—has thus elapsed.

In order to make it easier for the user to observe the necessary waiting time for the reaction of the body and/or its microorganisms, the composition and the quantity of the mass are selected so that, by the time the mass has been completely dissolved by the body fluid, the minimum time required to provoke the reaction of the body and/or its microorganisms has elapsed. When, therefore, the user sees that the composition has completely dissolved, the support can be removed and the desired medically relevant properties of the body fluid removed can be determined by the means mentioned above.

The invention is preferably used in determining the pH value of saliva, the metabolism of the microorganisms in the mouth having been stimulated beforehand by the substances present in the coating, more particularly by carbohydrates. The metabolism leads to a reduction in the pH value, i.e. to a more acidic surrounding medium. Accordingly, measurement of the pH value provides information as to the number of microorganisms in the mouth responsible for tooth decay. According to the inventors' studies, the risk of tooth decay can be determined relatively accurately. The measured pH values correlate strongly with the determined plaque indices which in turn are closely related to the risk of tooth decay.

However, the invention is not confined to the use of the test kit for determining the pH value of saliva. On the contrary, the test kit may be used for any provocation tests, i.e. for tests in which the human body—including its microorganisms—is first provoked into a reaction by the addition of certain substances. The body fluid altered by the reaction is then analyzed.

In one particularly advantageous embodiment of the invention for determining the risk of tooth decay, the mass contains at least one ingredient which stimulates the metabolism of the microorganisms in the mouth, more particularly a sugar-like substance or other carbohydrates, and optionally a sugar substitute. Sucrose and glucose are mentioned as examples of the sugar-like substance.

In addition, in the case of a test kit for determining the risk of tooth decay, the ingredients and quantity of the composition are selected so that the composition dissolves in the mouth in 1 to 10 minutes and preferably in 2 to 5 minutes.

After dissolution of the composition, more particularly in the form of a coating for the absorbent material, the user can be sure that the necessary waiting time for stimulation of an intensified metabolism of the microorganisms responsible for tooth decay has elapsed.

In another embodiment, the composition consists of a glaze which is essentially composed of the ingredient which stimulates the metabolism of the microorganisms and a fat as the binder. A coating such as this can be applied particularly economically to the absorbent material in the mass production of the test kit.

In the particular case of a test kit for determining tooth decay, the composition consists of flavorings and 17 to 45% by weight of glucose,
8 to 45% by weight of gelatins,
0 to 70% by weight of preservative,
2 to 10% by weight of sucrose.

This composition is preferably in the form of a coating of the absorbent material with a thickness of 0.1 to 0.5 mm and preferably 0.1 to 0.2 mm. This embodiment of the test kit ensures that a waiting time of 2 to 5 minutes has been observed after complete dissolution of the coating.

Consumer acceptance of the stick is improved if the composition contains flavorings. Lemon, lime, peppermint and eucalyptus flavours are mentioned as examples.

With waste disposal in mind, it is ecologically favorable if the support is in the form of a stick consisting essentially of wood.

If the absorbent material consists of individual fibres, more particularly of surgical cottonwool, individual fibres of the absorbent material are safely prevented from remaining behind in the mouth, which is unpleasant for the user, if the material is surrounded by a textile coated with the saliva-soluble mass. For ecological reasons, the textile is a cloth of natural fibres, preferably cotton.

Acceptance of the test kit, particularly among children, can be improved if the absorbent material is in the shape of an animal, an animal's head, a child's plaything or any other article attractive to children.

In a particularly inexpensive embodiment that is easy to handle by the consumer, the means for determining the pH value of the saliva removed is in the form of test paper for determining the pH value. Thus, a test zone may be provided which changes to different colors when liquids with different pH values are applied. Colored comparison boxes enable the pH value to be quickly and reliably determined. Corresponding test papers are inexpensive because they are mass-produced.

The present invention also relates to a process for analyzing saliva using the described test kit. According to the invention, the absorbent material and the composition are kept in the mouth until the coating has dissolved, after which the pH value of the saliva removed is determined with the relevant means. It is possible in this way to obtain information as to the microorganisms in the mouth and hence as to the risk of tooth decay, as already explained.

Finally, the present invention relates to an economic process for the production of the test kit according to the invention. In a preferred embodiment, the moistened absorbent material, more particularly surgical cottonwool, is first wound around one end of a stick, optionally compressed into a certain shape and, after drying of the stick, the end in question is dipped into a liquefied, more particularly molten, coating composition and, finally, the coating is left to harden.

BRIEF DESCRIPTION OF THE DRAWINGS

One example of embodiment of the invention is described in detail in the following with reference to the accompanying drawings, wherein:

FIG. 3 illustrates the dependence of the plaque index on oral hygiene.

DETAILED DESCRIPTION OF THE DRAWINGS

Figure 1:
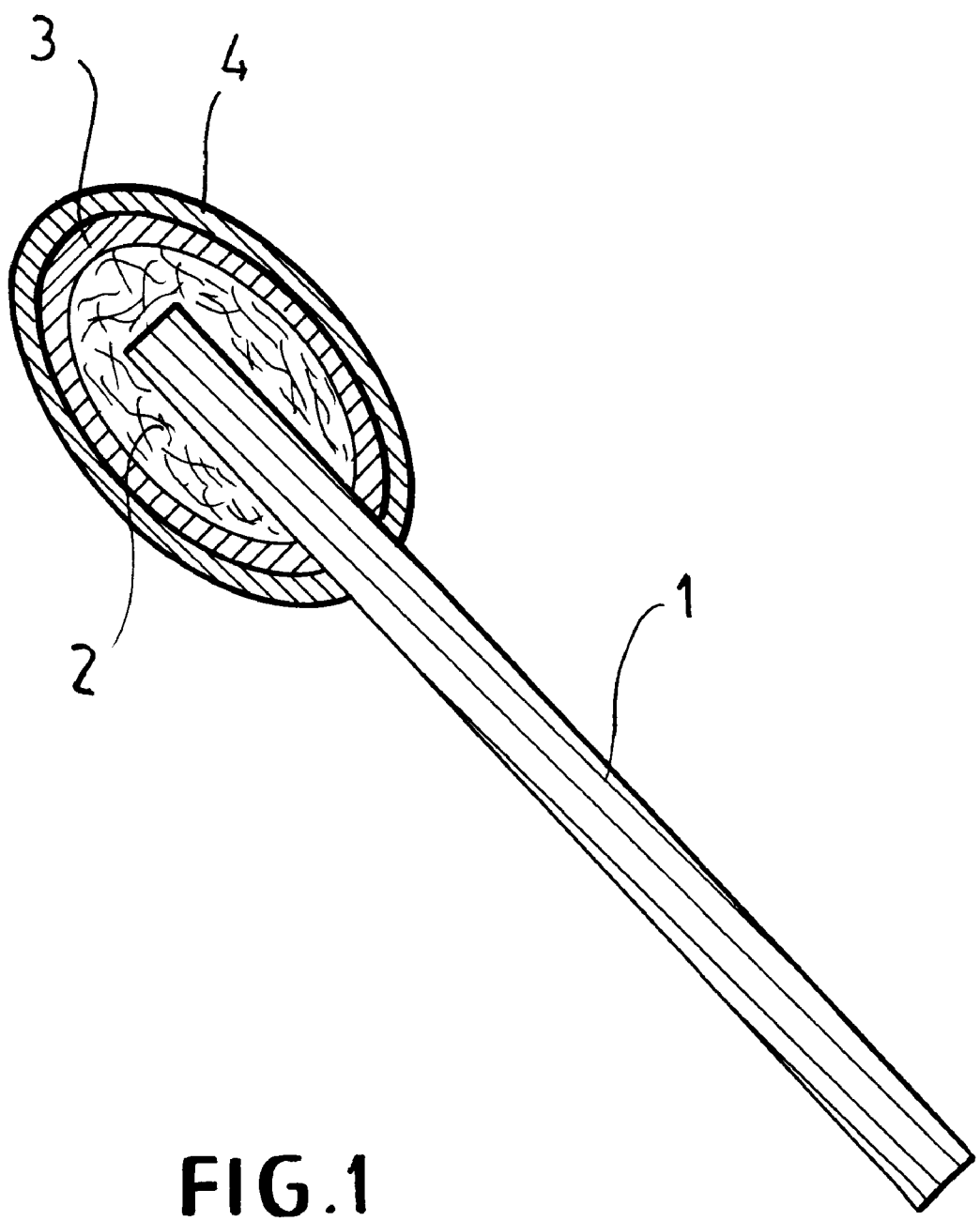
FIG. 1 is a cross-section through the stick of a test kit according to the invention.

One end of a wooden stick 1 shown in FIG. 1 is wrapped in surgical cottonwool 2. A cotton cloth 3 surrounds the cottonwool and thus prevents the detachment of individual fibres when the cottonwool comes into contact with the saliva. The cloth 3 is coated with a glaze 4 which contains the substance for stimulating the metabolism of the microorganisms and a fat as binder.

The glaze has the following composition:

48% by weight of glucose

40% by weight of gelatine

3% by weight of sodium benzoate as preservative

9% by weight of sucrose and flavorings (lemon, wild raspberry).

The coating has a thickness of 0.1 to 0.2 mm. The thickness of the coating is selected so that the coating dissolves in the mouth in about 3 minutes.

In the production of the stick, moist cottonwool is wound around one end of a wooden stick so that it adheres firmly to the wood. This step known from the production of cottonwool buds which are used for cleaning ears. After drying, the cotton cloth is applied and the end of the wooden stick is dipped into a glaze of the above-mentioned composition which has been liquefied by heating.

Figure 2:
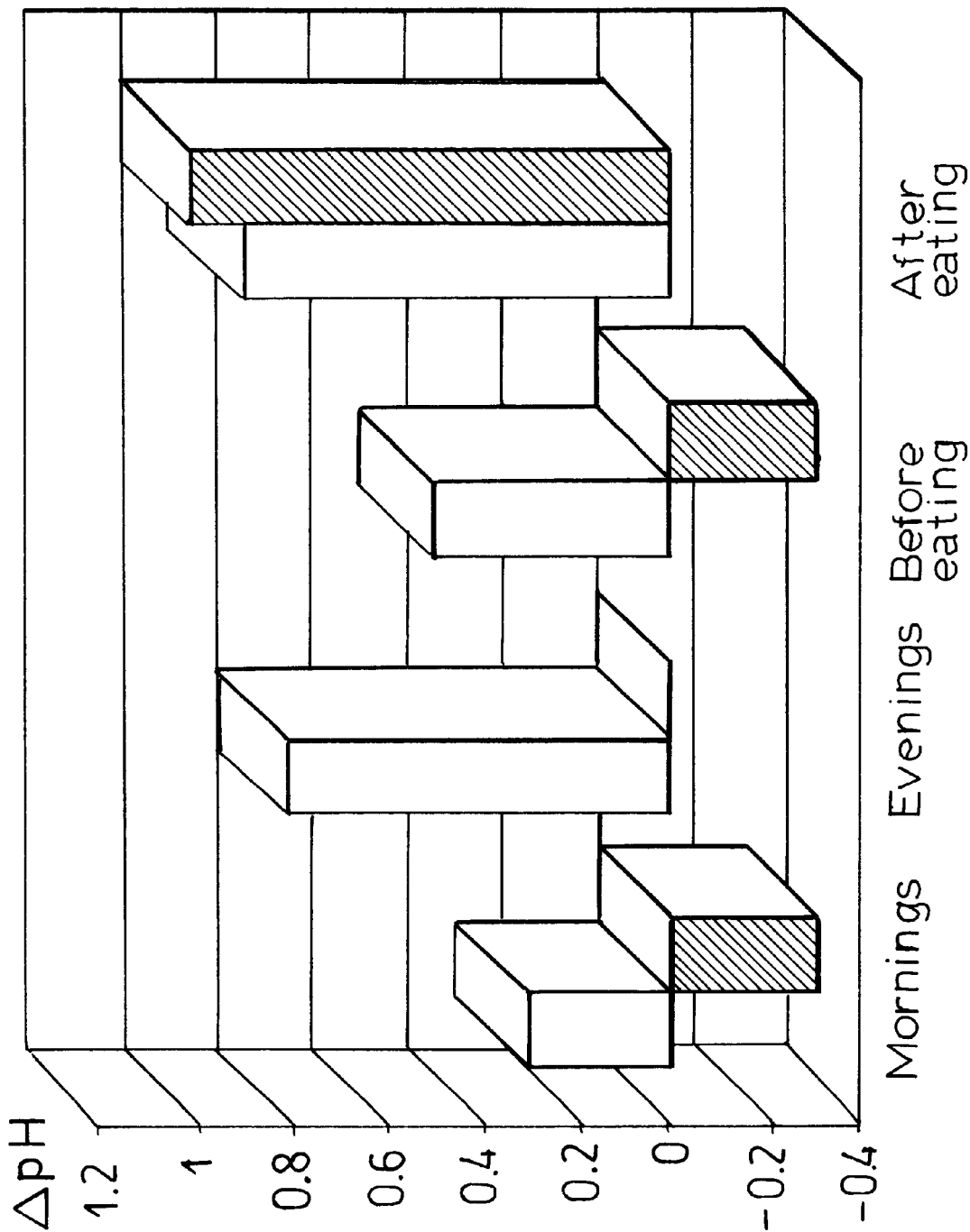
FIG. 2 is a graph of the pH value over the course of a day as a function of oral hygiene.

FIG. 2 shows the deviation of the pH value of the saliva from the neutral point (pH 7) as a function of oral hygiene (OH). The left-hand bars of each group show the value with oral hygiene and the right-hand bars the value without oral hygiene. Studies involving 100 volunteers revealed an average deviation in the pH of +0.8 to 7.8 in the evenings and one of only +0.3 to 7.3 in the mornings. The standard deviation was ±15%. The change in the pH value is attributable to the growth of the microorganisms and their metabolism at night. The same also applies to volunteers with average oral hygiene.

Distinct over-acidification occurs in the mornings and evenings. Rapid alkalization occurs after cleaning of the teeth and the reaction of the saliva glands, disappearing again quickly after eating. The over-acidification caused by the absence of oral hygiene or by inadequate oral hygiene correlates strikingly with the plaque indices determined, as shown by the graph in FIG. 3. The plaque index in percent is a measure of the presence of tartar. The thicker the tartar, the lower the plaque index.

If, now, in the test according to the invention the metabolism of the microorganisms is provoked by the sugars in the coating of the stick, the pH value of the saliva falls to an extent which is greater, the larger the number of harmful microorganisms responsible for tooth decay. Accordingly, measurement of the pH value after the addition of sugars or other carbohydrates provides information as to the risk of tooth decay, enables oral hygiene to be successfully monitored and, in addition, indicates whether there is any need for the teeth to be additionally cleaned.

To use the test kit, the stick mentioned above is removed from a test tube and placed in the mouth. After the pleasant-tasting coating has been completely dissolved by sucking, which takes about 3 minutes, the stick with the saliva-impregnated cottonwool bud is removed from the mouth. The moist cottonwool bud is rolled back and forth over a test strip until the strip changes color. By comparing the color with a color scale positioned beside the test strip, the pH value and hence the risk of tooth decay can be read off.

The test strip and the colour scale are preferably arranged at an easily accessible place on or inside the kit pack, for example on the inside of a folded paper or paperboard booklet.

What is claimed is:

1. A test kit for analyzing a patient's saliva to determine the patient's risk of tooth decay, which comprises:

(a) a support;

(b) an absorbent material in contact with said support and capable of removing saliva from the mouth and of absorbing the saliva;

(c) a composition coated on said absorbent material, said composition soluble in saliva and capable of reaction inside the mouth of the patient with the saliva to reduce the pH of the saliva; and (d) means for determining outside of the mouth of the patient the pH of the saliva reacted with the composition and absorbed by the absorbent material to determine the patient's risk of tooth decay.

2. The test kit defined in claim 1 wherein the composition coated on said absorbent material completely surrounds the absorbent material.

3. The test kit defined in claim 1 wherein the composition is so selected that by the time the composition has been completely dissolved in the body fluid, a minimum time required to provoke the reaction of the composition and the saliva in the patient's mouth has elapsed.

4. The test kit defined in claim 1 therein the composition is in the form of a glaze which consists of an ingredient which reacts with the microorganisms in the saliva in the patient's mouth and fat as a binder.

5. The test kit defined in claim 1 wherein the composition consists essentially of 17 to 45% by weight of glucose;

8 to 45% by weight of gelatine;

0 to 70% by weight of a preservative;

2 to 10% by weight of sucrose; and a flavoring.

6. The test kit defined in claim 1 wherein the support is a stick consisting essentially of wood.

7. The test kit defined in claim 1 wherein the absorbent material consists of individual fibers of surgical cottonwool, and is surrounded by a cotton cloth, on which is coated the composition soluble in saliva.

8. The test kit defined in claim 1 wherein the absorbent material is in the shape of an animal or an animal's head.

9. The test kit defined in claim 1 wherein the composition contains at least one ingredient which reacts with the saliva in the patient's mouth.

10. The test kit defined in claim 9 wherein the composition contains a carbohydrate and a sugar substitute.

11. The test kit defined in claim 11 wherein the composition dissolves in the saliva in the patient's mouth in 1 to 10 minutes.

12. The test kit defined in claim 11 wherein the composition dissolves in the saliva in the patient's mouth in 2 to 5 minutes.

13. The test kit defined in claim 11 wherein the composition is in the form of a coating on the absorbent material with a thickness of 0.1 to 0.5 mm.

14. The test kit defined in claim 13 wherein the thickness of the composition coated on the absorbent material is 0.1 to 0.2 mm.

15. The test kit defined in claim 11 wherein the means for determining outside of the mouth of the patient the pH of the saliva absorbed by the absorbent material is a test paper for determining pH value which is arranged on or in the kit pack.

16. The test kit defined in claim 15 wherein the means for determining outside of the mouth of the patient the pH of the saliva absorbed by the absorbent material further includes a color scale.

17. A process for analyzing a patient's saliva to determine the patient's risk of tooth decay, which comprises the steps of:

(a) absorbing saliva and removing the saliva from the patient's mouth by placing in the patient's mouth a test kit which comprises:

(1) a support;
(2) an absorbent material in contact with said support and capable of removing saliva from the patient's mouth and of absorbing the saliva; and
(3) a composition coated on said absorbent material, said composition soluble in saliva and capable of reaction inside the mouth of the patient with the saliva to reduce the pH of the saliva;

(b) allowing a reaction within the patient's mouth of said composition and the saliva;

(c) following step (b), determining outside of the mouth of the patient the pH of the saliva reacted with the composition and absorbed by the absorbent material during step (b); and (c) analyzing the patient's risk of tooth decay based upon the pH of the saliva determined in step (b).

* * * * *